United States Patent [19]
Givens et al.

[11] Patent Number: 6,101,449
[45] Date of Patent: Aug. 8, 2000

[54] METHOD FOR PREDICTING THE PRESENCE OF CONGENITAL AND THERAPEUTIC CONDITIONS FROM COAGULATION SCREENING ASSAYS

[75] Inventors: Thomas B. Givens, Rougemont; Paul Braun, Durham; Timothy J. Fischer, Raleigh, all of N.C.

[73] Assignee: Akzo Nobel N.V., Arnhem, Netherlands

[21] Appl. No.: 08/859,773

[22] Filed: May 21, 1997

Related U.S. Application Data

[63] Continuation of application No. 08/477,839, Jun. 7, 1995, Pat. No. 5,708,591.

[51] Int. Cl.[7] ..................................................... G01N 21/00
[52] U.S. Cl. ............................... 702/22; 702/28; 702/30; 702/32; 395/500.32
[58] Field of Search ........................... 702/22, 23, 27–32, 702/128, 131, 139, 179, 180, 183, FOR 115–FOR 119, FOR 170, FOR 171, FOR 131; 436/66, 43, 47–50, 54, 55, 69, 174, 164, 171, 180, 805, 809, 808, 909; 422/50, 61–67, 68.1, 73, 82.05, 105; 364/528.01, 578; 382/133, 134, 156–159; 356/39, 40, 42; 706/924, 21, 20; 435/13; 73/64.43; 377/10, 11; 395/500.32, 500.33; 514/822, 834; 700/266, 268

[56] References Cited

U.S. PATENT DOCUMENTS

| 3,307,392 | 3/1967 | Owen et al. ........................... 73/64.43 |
| 3,458,287 | 7/1969 | Gross et al. .............................. 436/69 |

(List continued on next page.)
(List continued on next page.)

FOREIGN PATENT DOCUMENTS

| 115459 | 1/1983 | European Pat. Off. . |
| 434377 | 12/1989 | European Pat. Off. . |

(List continued on next page.)

OTHER PUBLICATIONS

Koagulab 16–S Plus Graphics, Koagulab 32–S Coagulation System, Graphics Binder pp. 2,3,5,6,8,9,11–17,19–21,23, no date.

Ortho Factor VIII:C Deficient Plasma, Ortho Diagnostic Systems, Inc. pp. 1–2 1988 (Sep. 1988).

(List continued on next page.)

*Primary Examiner*—Hal Wachsman
*Attorney, Agent, or Firm*—Gregory R. Muir

[57] ABSTRACT

A method and apparatus are disclosed for predicting the presence of at least one congenital or acquired imbalances or therapeutic condition associated with thrombosis/hemostasis from at least one time-dependent measurement profile. At least one time-dependent measurement in a sample is performed and a respective property of sample is measured over time so as to derive a time-dependent measurement profile. A set of a plurality of predictor variables are defined which sufficiently define the data of the time-dependent measurement profile. A model is then derived that represents the relationship between the congenital or acquired imbalance or therapeutic condition, and the set of predictor variables. Subsequently, the model is utilized to predict the existence of the congenital or acquired imbalance or therapeutic condition in a sample.

48 Claims, 14 Drawing Sheets

U.S. PATENT DOCUMENTS

| | | | |
|---|---|---|---|
| 3,658,480 | 4/1972 | Kane et al. | 436/69 |
| 4,047,890 | 9/1977 | Eichelberger et al. | 436/69 |
| 4,199,748 | 4/1980 | Bacus | 382/134 |
| 4,217,107 | 8/1980 | Saito Yukio et al. | 436/69 |
| 4,279,616 | 7/1981 | Saito et al. | 436/69 |
| 4,289,498 | 9/1981 | Baughman et al. | 436/34 |
| 4,766,083 | 8/1988 | Miyashita et al. | 436/517 |
| 4,965,725 | 10/1990 | Rutenbeng | 706/924 |
| 4,998,535 | 3/1991 | Selker et al. | 600/509 |
| 5,156,974 | 10/1992 | Grossman et al. | 436/69 |
| 5,169,786 | 12/1992 | Carrol et al. | 436/69 |
| 5,218,529 | 6/1993 | Meyer et al. | 702/28 |
| 5,388,164 | 2/1995 | Yonekawa et al. | 382/134 |
| 5,473,732 | 12/1995 | Chang | 706/59 |
| 5,553,616 | 9/1996 | Ham et al. | 706/924 |
| 5,563,983 | 10/1996 | Nozaki et al. | 706/21 |
| 5,591,403 | 1/1997 | Gavin et al. | 422/73 |
| 5,708,591 | 1/1998 | Givens et al. | 702/22 |
| 5,716,795 | 2/1998 | Matschiner | 435/13 |

FOREIGN PATENT DOCUMENTS

| | | |
|---|---|---|
| 525273 | 8/1991 | European Pat. Off. . |
| 841566 | 11/1996 | European Pat. Off. . |
| 2364453 | 9/1976 | France . |
| 2635081 | 7/1976 | Germany . |
| 3502878 | 1/1985 | Germany . |
| 59/203959 | 5/1983 | Japan . |
| 60/114768 | 11/1983 | Japan . |
| 61/272655 | 5/1985 | Japan . |
| 05/180835 | 12/1991 | Japan . |
| 06/027115 | 7/1992 | Japan . |
| 06/249855 | 2/1993 | Japan . |
| 10/104239 | 9/1996 | Japan . |
| 2012877 | 4/1991 | Russian Federation . |
| 2070327 | 12/1992 | Russian Federation . |
| 2061953 | 3/1993 | Russian Federation . |
| 590665 | 11/1976 | U.S.S.R. . |
| 1076086 | 12/1982 | U.S.S.R. . |
| 1691741 | 8/1989 | U.S.S.R. . |
| 1777089 | 6/1990 | U.S.S.R. . |
| 2005014 | 9/1977 | United Kingdom . |
| WO 8606840 | 1/1983 | WIPO . |
| WO 9108460 | 1/1989 | WIPO . |
| WO 9101383 | 7/1989 | WIPO . |
| WO 9101497 | 7/1989 | WIPO . |
| WO 9102812 | 8/1989 | WIPO . |
| WO 9116453 | 4/1990 | WIPO . |
| WO 9307491 | 10/1991 | WIPO . |
| WO 9407145 | 9/1992 | WIPO . |
| WO 9411714 | 11/1992 | WIPO . |
| WO 9416095 | 1/1993 | WIPO . |
| WO 9505590 | 8/1993 | WIPO . |
| WO 9508121 | 9/1993 | WIPO . |
| WO 9530154 | 4/1994 | WIPO . |
| WO 9614581 | 11/1994 | WIPO . |
| WO 9621740 | 1/1995 | WIPO . |
| WO 9641291 | 2/1995 | WIPO . |
| WO95 05590 | 2/1995 | WIPO . |
| WO 9642018 | 6/1995 | WIPO . |
| WO 9720066 | 11/1995 | WIPO . |
| WO 9734698 | 3/1996 | WIPO . |

OTHER PUBLICATIONS

American Diagnostica Inc. 3X15 Test Kit for Determination of Plasma Protein C Activity Using a Clotting End–Point, pp. 1,2. Feb. 1989.

Package insert for Ortho Brain Thromboplastic Reagent, pp. 1–7. (no date).

The American Society of Hematology, 31st Annual Meeting Abstract Reproduction Form, p. 1. (no date).

American Clinical Laboratory (Apr. 1989) pp. 1–5.

The Clot Signature and New Aspects in Coagulation Testing, Ortho Diagnostic Systems, Inc. (Aug. 1989) pp. 1–20.

J.W. Furlong et al., *Am. J. Clin. Pathol.*, 96:1:134–141, Jul. 1991.

J. Boone et al., *Neural Networks in Radiologic Diagnosis*, 25:9:1013–1023 (no date).

M.A. Khanin et al., *J. Theor. Biol.*, 136:127–134 (1989). (no month).

P. Baumann et al., *Haemostasis*, 19:309–321 (1989). (no month).

C.C. Heuck et al., *Haemostasis*, 21:10–18 (1991). (no month).

J.F. Hoffman et al., "The Coag–A–Mate RA4 Fibrinogen Assay" Organon Teknika pp. 3–7, 1990 (no month).

B. Pohl et al., *Haemostasis*, 24:325–337 (1994). (no month).

A.L. Astion et al., *Arch Pathol Lab Med*, 116:995–1001 (1992).

W.R.M. Dassen et al., *Journal of Electrocardiology*, 23 (Supp.) 201–202 (no date).

J.A. Swets et al.., *Science*, 240:1285–1293 (Jun. 3, 1988).

D.A. Bluestein et al., *Nurse Practitioner*, 17:7:39–45 (Jul. 1991).

J.T. Brandt et al., *Arch Pathol Lab Med*, 115:109–114 (Feb. 1991).

I. Talstad, *Haemostasis*, 23:19–25, 1993. (no month).

E. Baum et al., *MIT Press*, 81–89, 1989 (no month).

M.L. Asiton et al., *Clin. Chem.*, 39/9 1998–2004, (1993). (no month).

M.H. Zweig et al., *Clin. Chem.*, 39/4 561–577 (1993). (no month).

C.R. Schweiger et al. *Clin. Chem.*, 39/9 1966–1971 (1993). (no month).

J. Sweeney et al., Journal of the American Society of Hematology, 76:10(1) Poster #1745, Nov. 15, 1990, p. 439.

J. Sweeney et al., Journal of the American Society of Hematology, 74:7(1) Poster #1509, Nov. 1989, p. 395.

Sabbatini, R.M.E, "Neural Networks for Classification and Pattern Recognition of Biological Signals" *Conf. Of the Engineering in Medicine and Biology Society, U.S., New York*, IEEE, vol. Conf. 15, pp. 265–266, Oct. 28 1993.

Pattichis C.S. et al., "Efficient Training of Neural Network Models in Classification of Electromyographic Data" *Medical and Biological and Computer*, GB, Peter Peregrinus Ltd., col. 33, no. 3, p. 499, May 1995.

| Hidden Layer Size | Error | | |
|---|---|---|---|
| | $E_{tr}$ | $E_{DV}$ | $\varphi_{ODB}$ |
| 2 | 0.384 | 0.376 | 0.848 |
| 4 | 0.386 | 0.354 | 0.835 |
| 6 | 0.341 | 0.328 | 0.875 |
| 8 | 0.358 | 0.327 | 0.857 |
| 10 | 0.346 | 0.325 | 0.856 |
| 12 | 0.347 | 0.322 | 0.855 |

Predictor Variables

| Predictor Variable | Description |
|---|---|
| $pv_{j1} = \left(\frac{dT}{dt}\right)_{min}$ | minimum of the first derivative |
| $pv_{j2} = t$ at $\left(\frac{dT}{dt}\right)_{min}$ | time index of the minimum of the first derivative |
| $pv_{j3} = \left(\frac{d^2T}{dt^2}\right)_{min}$ | minimum of the second derivative |
| $pv_{j4} = t$ at $\left(\frac{d^2T}{dt^2}\right)_{min}$ | index of the minimum of the second derivative |
| $pv_{j5} = \left(\frac{d^2T}{dt^2}\right)_{max}$ | maximum of the second derivative |
| $pv_{j6} = t$ at $\left(\frac{d^2T}{dt^2}\right)_{max}$ | index of the maximum of the second derivative |
| $pv_{j7} = T_{t_0} - T_{t_R}$ | overall change in transmittence during the reaction |

METHOD FOR PREDICTING THE PRESENCE OF CONGENITAL AND THERAPEUTIC CONDITIONS FROM COAGULATION SCREENING ASSAYS

This application is a continuation of U.S. patent application Ser. No. 08/477,389 to Givens et al. filed Jun. 7, 1995, (now U.S. Pat. No. 5,708,591) the subject matter of which is incorporated herein by reference. This application is also related to the following publications, the subject matter of each also being incorporated herein by reference:

1. B. Pohl, C. Beringer, M. Bomhard, F. Keller, The quick machine—a mathematical model for the extrinsic activation of coagulation, *Haemostasis,* 24, 325–337 (1994).

2. J. Brandt, D. Triplett, W. Rock, E. Bovill, C. Arkin, Effect of lupus anticoagulants on the activated partial thromboplastin time, *Arch Pathol Lab Med,* 115, 109–14 (1991).

3. I. Talstad, Which coagulation factors interfere with the one-stage prothrombin time?, *Haemostasis,* 23, 19–25 (1993).

4. P. Baumann, T. Jurgensen, C. Heuck, Computerized analysis of the in vitro activation of the plasmatic clotting system, *Haemostasis,* 19, 309–321 (1989).

5. C. Heuck, P. Baumann, Kinetic analysis of the clotting system in the presence of heparin and depolymerized heparin, *Haemostasis,* 21, 10–18 (1991).

6. M. Astion and P. Wilding, The application of back-propagation neural networks to problems in pathology and laboratory medicine, *Arch Pathol Lab Med,* 116, 995–1001 (1992).

7. M. Astion, M. Wener, R. Thomas, G. Hunder, and D. Bloch, Overtraining in neural networks that interpret clinical data, *Clinical Chemistry,* 39, 1998–2004 (1993).

8. J. Furlong, M. Dupuy, and J. Heinsimer, Neural network analysis of serial cardiac enzyme data, *A.J.C.P.,* 96, 134–141 (1991).

9. W. Dassen, R. Mulleneers, J. Smeets, K. den Dulk, F. Cruz, P. Brugada, and H. Wellens, Self-learning neural networks in electrocardiography, *J. Electrocardiol,* 23, 200–202 (1990).

10. E. Baum and D. Haiissler, What size net gives valid generalization? *Advances in Neural Information Processing Systems,* Morgan Kauffman Publishers, San Mateo, Calif., 81–90 (1989).

11. A. Blum, Neural Networks in C++, John Wiley & Sons, New York, (1992).

12. S. Haykin, *Neural Networks A Comprehensive Foundation,* Macmillan College Publishing Company, New York, (1994).

13. J. Swets, Measuring the accuracy of diagnostic systems, Science, 240, 1285–1293 (1988).

14. M. Zweig and G. Campbell, Receiver-operating characteristic (ROC) plots: a fundamental evaluation tool in clinical medicine, *Clinical Chemistry,* 39, 561–577 (1993).

15. D. Bluestein, L. Archer, The sensitivity, specificity and predictive value of diagnostic information: a guide for clinicians, *Nurse Practitioner,* 16, 39–45 (1991).

16. C. Schweiger, G. Soeregi, S. Spitzauer, G. Maenner, and A. Pohl, Evaluation of laboratory data by conventional statistics and by three types of neural networks, *Clinical Chemistry,* 39, 1966–1971 (1993).

BACKGROUND OF THE INVENTION

Blood clots are the end product of a complex chain reaction where proteins form an enzyme cascade acting as a biologic amplification system. This system enables relatively few molecules of initiator products to induce sequential activation of a series of inactive proteins, known as factors, culminating in the production of the fibrin clot. Mathematical models of the kinetics of the cascade's pathways have been previously proposed.

In Pohl et al. The quick machine—a mathematical model for the extrinsic activation of coagulation, *Haemostasis,* 24, 325–337 (1994), a dynamic model of the extrinsic coagulation cascade was described where data were collected for 20 samples using quick percent, activated partial thromboplastin time (APT), thrombin time (TT), fibrinogen, factor (F) II, FV, FVII, FX, anti-thrombin III (ATIII), and factor degradation product (FDP) assays. These data were used as input to the model and the predictive output compared to actual recovered prothrombin time (PT) screening assay results. The model accurately predicted the PT result in only 11 of 20 cases. These coagulation cascade models demonstrate: (1) the complexity of the clot formation process, and (2) the difficulty in associating PT clot times alone with specific conditions.

Thrombosis and hemostasis testing is the in vitro study of the ability of blood to form clots and to break clots in vivo. Coagulation (hemostasis) assays began as manual methods where clot formation was observed in a test tube either by tilting the tube or removing fibrin strands by a wire loop. The goal was to determine if a patient's blood sample would clot after certain materials were added. It was later determined that the amount of time from initiation of the reaction to the point of clot formation in vitro is related to congenital disorders, acquired disorders, and therapeutic monitoring. In order to remove the inherent variability associated with the subjective endpoint determinations of manual techniques, instrumentation has been developed to measure clot time, based on (1) electromechanical properties, (2) clot elasticity, (3) light scattering, (4) fibrin adhesion, and (5) impedance. For light scattering methods, data is gathered that represents the transmission of light through the specimen as a function of time (an optical time-dependent measurement profile).

Two assays, the PT and APT, are widely used to screen for abnormalities in the coagulation system, although several other screening assays can be used, e.g. protein C, fibrinogen, protein S and/or thrombin time. If screening assays show an abnormal result, one or several additional tests are needed to isolate the exact source of the abnormality. The PT and APT assays rely primarily upon measurement of time required for clot time, although some variations of the PT also use the amplitude of the change in optical signal in estimating fibrinogen concentration.

Blood coagulation is affected by administration of drugs, in addition to the vast array of internal factors and proteins that normally influence clot formation. For example, heparin is a widely-used therapeutic drug that is used to prevent thrombosis following surgery or under other conditions, or is used to combat existing thrombosis. The administration of heparin is typically monitored using the APT assay, which gives a prolonged clot time in the presence of heparin. Clot times for PT assays are affected to a much smaller degree. Since a number of other plasma abnormalities may also cause prolonged APT results, the ability to discriminate between these effectors from screening assay results may be clinically significant.

Using a sigmoidal curve fit to a profile, Baumann, et al Computerized analysis of the in vitro activation of the plasmatic clotting system, *Haemostasis,* 19, 309–321. (1989) showed that a ratio of two coefficients was unique for a select group of blood factor deficiencies when fibrinogen was artificially maintained by addition of exogenous fibrinogen to a fixed concentration, and that same ratio also correlates heparin to FII deficiency and FXa deficiencies. However, the requirement for artificially fixed fibrinogen makes this approach inappropriate for analysis of clinical specimens. The present invention makes it possible to predict a congenital or acquired imbalance or therapeutic condition for clinical samples from a time-dependent measurement profile without artificial manipulation of samples.

The present invention was conceived of and developed for predicting the presence of congenital or acquired imbalances or therapeutic conditions of an unknown sample based on one or more time-dependent measurement profiles, such as optical time-dependent measurement profiles, where a set of predictor variables are provided which define characteristics of profile, and where in turn a model is derived that represents the relationship between a congenital or acquired imbalance or therapeutic condition and the set of predictor variables (so as to, in turn, utilize this model to predict the existence of the congenital or acquired imbalance or therapeutic condition in the unknown sample).

SUMMARY OF THE INVENTION

The present invention is directed to a method and apparatus for predicting the presence of at least one congenital or acquired imbalance or therapeutic condition from at least one time-dependent measurement profile. The method and apparatus include a) performing at least one assay on an unknown sample and measuring a respective property over time so as to derive a time-dependent measurement profile, b) defining a set of predictor variables which sufficiently define the data of the time-dependent profile, c) deriving a model that represents the relationship between a diagnostic output and the set of predictor variables, and d) utilizing the model to predict the existence of a congenital or acquired imbalance or therapeutic condition in the unknown sample relative to the diagnostic output. In one embodiment, training data is provided by performing a plurality of assays on known samples, the model is a multilayer perceptron, the relationship between the diagnostic output and the set of predictor variables is determined by at least one algorithm, and the at least one algorithm is a back propagation learning algorithm. In a second embodiment of the present invention, the relationship between the diagnostic output and the set of predictor variables is derived by a set of statistical equations.

Also in the present invention, a plurality of time-dependent measurement profiles are derived, which time-dependent measurement profiles can be optical time-dependent measurement profiles such as ones provided by a automated analyzer for thrombosis and hemostasis, where a plurality of optical measurements are taken over time, and where the plurality of optical measurements are normalized. The optical profiles can include one or more of a PT profile (Prathrombin Time Profile), a fibrinogen profile, an APT profile (Activated Partial Thromboplastin Time profile), a TT profile (Thrombin Time profile), a protein C profile, a protein S profile and a plurality of other assays associated with congenital or acquired imbalances or therapeutic conditions.

BRIEF DESCRIPTION OF THE DRAWINGS

FIG. 9 is a Table comparing hidden layer size with prediction error;

FIG. 13 is a chart listing examples of predictor variables use in the present invention.

DESCRIPTION OF THE PREFERRED EMBODIMENTS

Figure 14:
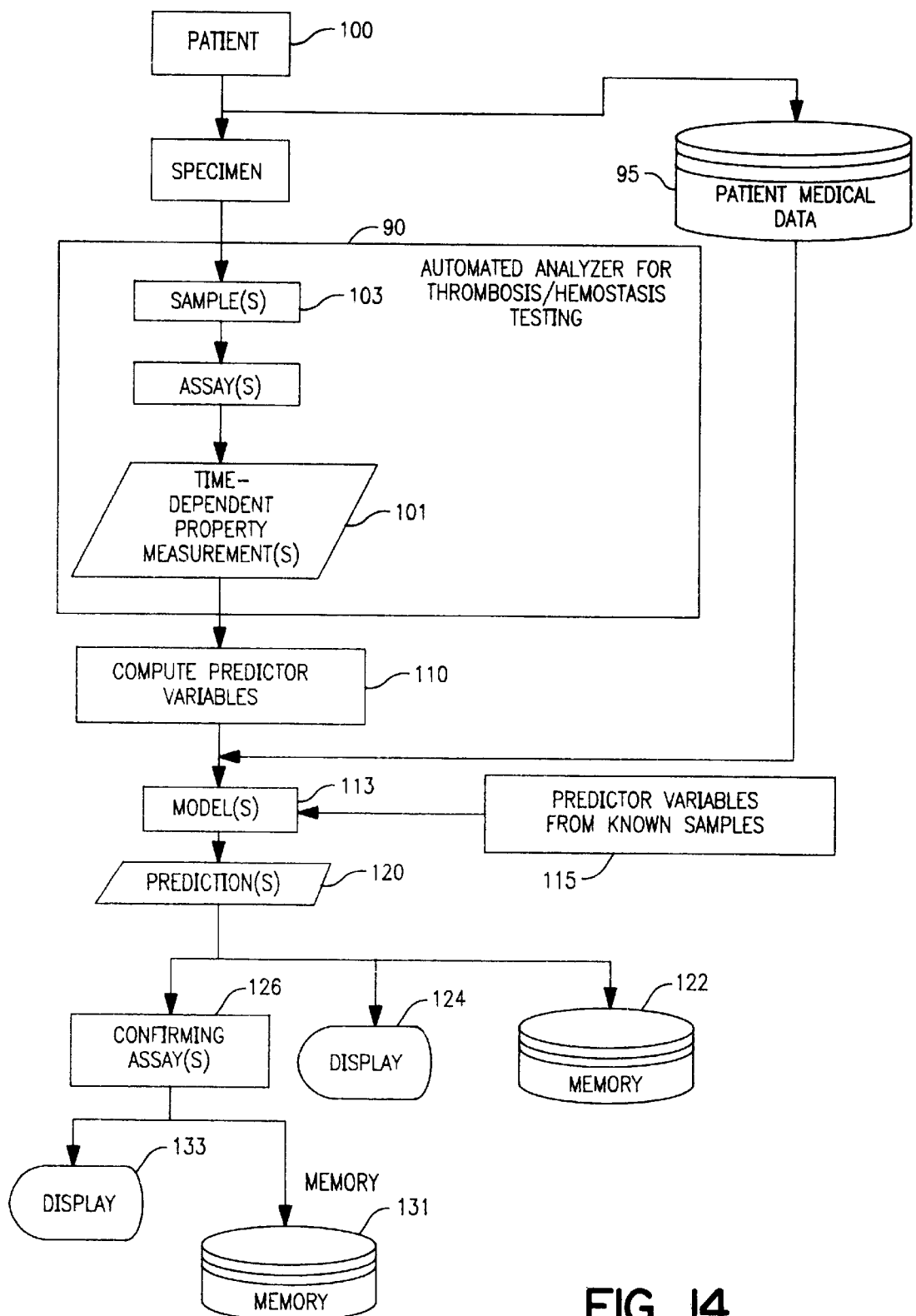
FIG. 14 is a chart illustrating key aspects of the present invention.

In the present invention, both a method and apparatus are provided for predicting the presence of at least one congenital or acquired imbalance or therapeutic condition. As can be seen in FIG. 14, one or more time-dependent measurements (101) are performed on an unknown sample (103). The term "time-dependent measurement" is referred to herein to include measurements derived from assays (e.g. PT, APT, fibrinogen, protein C, protein S, TT, ATIII, plasminogen and factor assays). The terms "unknown sample" and "clinical sample" refer to a sample, such as one from a medical patient (100), where a congenital or acquired imbalance or therapeutic condition associated with thrombosis/hemostasis is not known (or, if suspected, has not been confirmed). In the present invention, a coagulation property is measured over time so as to derive a time-dependent measurement profile. In a preferred embodiment, the time-dependent measurement is an optical measurement for deriving an optical profile. For example, a PT profile, a fibrinogen profile, a TT profile, an APT profile and/or variations thereof can be provided where, an unknown sample is analyzed for clot formation based on light transmittance over time through the unknown sample. In another preferred embodiment, two (or more) optical profiles are provided, such as both a PT profile and an APT profile.

After the time-dependent measurement profiles are provided, a set of predictor variables are defined (110) which sufficiently define the data of the time-dependent profile. One or more predictor variables comprise the set. And, in one embodiment, three or more, and in a preferred embodiment, four or more predictor variables were found to desirably make up the set. It was found that the characteristics of the time-dependent measurement profile could best be defined by one or more predictor variables, including the minimum of the first derivative of the optical profile, the time index of this minimum, the minimum of the second derivative of the optical profile, the time index of this minimum, the maximum of the second derivative, the time index of this maximum, the overall change in transmittance during the time-dependent measurement, clotting time, slope of the optical profile prior to clot formation, and slope of the optical profile after clot formation.

After defining the set of predictor variables, a model (113) is derived which represents the relationship between a congenital or acquired imbalance or therapeutic condition and the set of predictor variables. This model can be derived from a neural network in one embodiment of the present invention. In another embodiment, the model is derived via a set of statistical equations.

Neural networks represent a branch of artificial intelligence that can be used to learn and model complex, unknown systems given some known date (115) from which it can train. Among the features of neural networks that make them an attractive alternative for modeling complex systems are:

1. They can handle noisy data well and recognize patterns even when some of the input data are obscured or missing.
2. It is unnecessary to determine what factors are relevant a priori since the network will determine during the training phase what data are relevant, assuming there are at least some meaningful parameters in the set.

Figure 1:
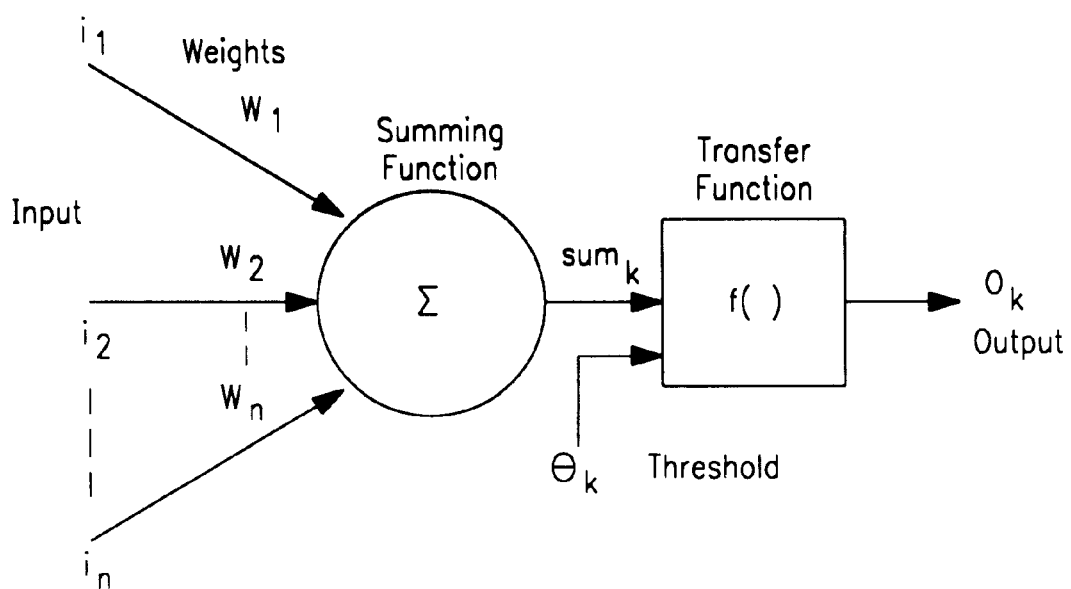
FIG. 1 is a general neuron diagram relating to the embodiment of the present invention utilizing a neural network.

Neural networks are formed from multiple layers of interconnected neurons like that shown in FIG. 1. Each neuron has one output and receives input $i_1 \ldots i_n$ from multiple other neurons over connecting links, or synapses. Each synapse is associated with a synaptic weight, $w_j$. An adder $\Sigma$ or linear combiner sums the products of the input signals and synaptic weights $i_j * w_j$. The linear combiner output $sum_1$ and $\theta_1$ (a threshold which lowers or a bias which raises the output) are the input to the activation function f( ). The synaptic weights are learned by adjusting their values through a learning algorithm.

After deriving the model (113), whether based on neural networks or statistical equations, the model is utilized to predict (120) the existence of a congenital or acquired imbalance or therapeutic condition in the unknown sample relative to the time-dependent measurement profile(s). As such, a congenital or acquired imbalance or therapeutic condition can be predicted. Conditions which can be predicted as being abnormal in the present invention can include, among others, a) factor deficiencies, e.g. fibrinogen, Factors II, V, VII, VIII, IX, X, XI and XII, as well as ATIII, plasminogen, protein C, protein S, etc., b) therapeutic conditions, e.g. heparin, coumadin, etc., and c) conditions such as lupus anticoagulant. In one embodiment of the present invention, the method is performed on an automated analyzer (90). The time-dependent measurement profile, such as an optical data profile, can be provided automatically by the automated analyzer, where the unknown sample is automatically removed by an automated probe from a sample container to a test well, one or more reagents are automatically added to the test well so as to initiate the reaction within the sample. A property over time is automatically optically monitored so as to derive the optical profile. The predicted congenital or therapeutic condition (120) can be automaticall stored in a memory (122) of an automated analyzer and/or displayed (124) on the automated analyzer, such as on a computer monitor, or printed out on paper. As a further feature of the invention, if the predicted congenital or acquired imbalance or therapeutic condition is an abnormal condition, then one or more assays for confirming the existence of the abnormal condition (126) are performed on the automated analyzer. In fact, in a preferred embodiment, the one or more confirming assays are automatically ordered and performed on the analyzer once the predicted condition is determined, with the results of the one or more confirming assays being stored in a memory (131) of the automated analyzer and/or displayed (133) on the analyzer. Also, where the unknown sample is from a medical patient, both the derived model and other patient medical data (95) can be used for predicting the imbalance/condition. If a monitoring system is used, a plurality of optical measurements at one or more wavelengths can be taken over time so as to derive the optical profile, with the optical measurements corresponding to changes in light scattering and/or light absorption in the sample. Also, the plurality of optical measurements can each be normalized to a first optical measurement. If the time-dependent measurement is an optical profile, this can be provided automatically by an analyzer, where a sample is automatically removed by an automated probe from a sample container to a test well, one or more reagents are automatically added to the test well so as to initiate the property changes within the sample, and the development of the property over time is automatically optically monitored so as to derive the optical data profile. And, the predictor variables can be a plurality of variables, three or more predictor variables, or more than three predictor variables.

EXAMPLE 1

Prediction of Heparin in Sample

This example shows a set of predictor variables that adequately describe screening assay optical profiles, develops an optimal neural network design, and determines the predictive capabilities of an abnormal condition associated with thrombosis/hemostasis (in this case for the detection of heparin) with a substantial and well-quantified test data set.

Simplastin™ L (tissue thromboplastin reagent for determination of Prothrobin Time in human plasma), Platelin™ L (a phospholipid reagent with particulate activators and a calcium chloride reagent for determination of Activated Partial Thromboplastin Time in human plasma), calcium chloride solution (0.025 M), imidazole buffer were obtained from Organon Teknika Corporation, Durham, N.C., 27712, USA. All plasma specimens were collected in 3.2% or 3.80% sodium citrate in the ratio of one part anticoagulant to nine parts whole blood. The tubes were centrifuged at 2000 g for 30 minutes and then decanted into polypropylene tubes and stored at –80° C. until evaluated. 757 specimens were prepared from 200 samples. These specimens were tested by the following specific assays: FII, FV, FVII, FVIII, FIX, FX, FXI, FXII, heparin, fibrinogen, plasminogen, protein C, and AT-III. Samples represented normal patients, a variety of deficiencies, and therapeutic conditions. Of the specimen population 216 were positive for heparin determined by a heparin concentration greater than 0.05 units/ml measured with a chromogenic assay specific for heparin. The remaining specimens, classified as heparin-negative, included normal specimens, a variety of single or multiple factor deficiencies, and patients receiving other therapeutic drugs. Positive heparin samples ranged to 0.54 units/ml.

PT and APT screening assays were performed on each specimen utilizing two automated analyzers (MDA™ 180s) and multiple reagent and plasma vials (Organon Teknika Corporation, Durham N.C. 27712, USA ) over a period of five days. When clot-based coagulation assays are performed by an automated optically-based analyzer such as the MDA 180, data are collected over time that represents the normalized level of light transmission through a sample as a clot forms (the optical profile). As the fibrin clot forms, the transmission of light is decreased. The optical profile was stored from each test.

Figure 2:
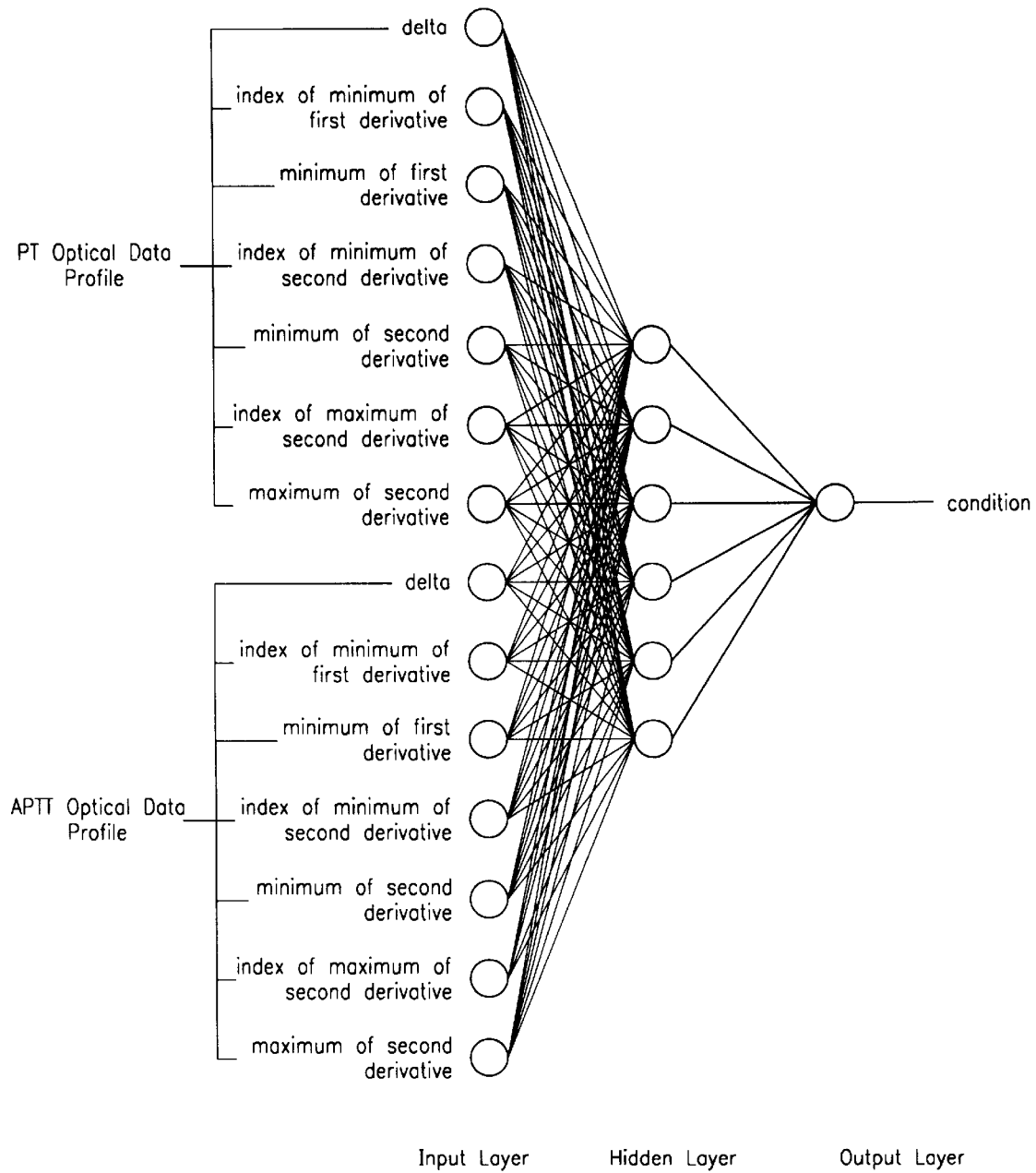
FIG. 2 is a diagram of a multilayer perceptron for predicting congenital or acquired imbalances or therapeutic conditions, relating to the neural network embodiment of the present invention.

The network configuration chosen, a multilayer perceptron (MLP) maps input predictor variables from the PT and APT screening assays to one output variable (see FIG. 2) which represents a single specified condition. A similar network was also employed for PT-only variables and APT-only variables. This specific MLP consists of three layers: the input layer, one hidden layer, and the output layer.

Figure 3:
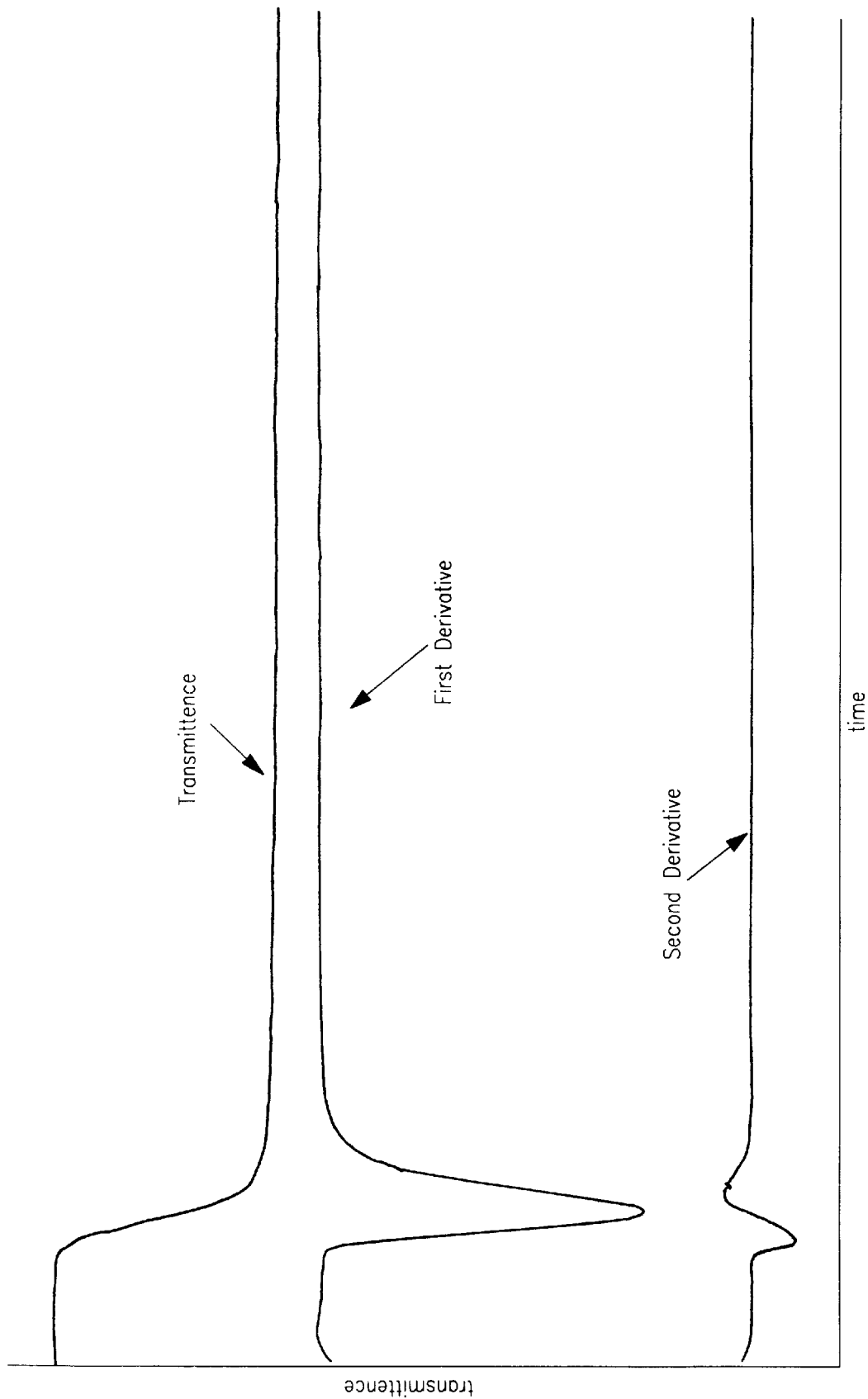
FIG. 3 is an optical profile with first and second derivatives of a normal clotting sample.

A normal optical profile is shown in FIG. 3. The set of predictor variables were chosen with the intent of describing optical profiles as completely as possible with a minimum number of variables. They are summarized in Table 1 where t is time from initiation of reaction, T is normalized light transmission through the reaction mixture, and $pv_{jk}$ is the kth predictor variable of assay j.

The predictor variables were scaled to values between 0 and 1, based on the range of values observed for each variable for assay type k $$i_j = f(pv_{jk},(pv_{j-n,k})_{min},(pv_{j-n,k})_{max}).$$

The input variable set includes $i_{1...7}$ for both a PT assay and APT assay for each specimen. For known output variable values, heparin samples with results of greater than 0.05 units/ml were considered positive and assigned a value of 1 while negative samples were assigned a value of 0.

As the ratio of training set sample to the number of weights in a network decreases, the probability of generalizing decreases, reducing the confidence that the network will lead to correct classification of future samples taken from the same distribution as the training set. Thus, small samples sizes, then can lead to artificially high classification rates. This phenomenon is known as overtraining. In order to achieve a true accuracy rate of 80%, a guideline for the number of samples in the training set is approximately five times the number of weights in the network. For most of this work, a 14-6-1 network was used, leading to an upward bound on the sample size of O(450). To monitor and evaluate the performance of the network and its ability to generalize, a cross-validation set is processed at the end of each training epoch. This cross-validation set is a randomly determined subset of the known test set that is excluded from the training set.

Once the input predictor variables and output values were determined for all specimen optical profiles, the 757 sets of data were randomly distributed into two groups: 387 were used in the training set and 370 were used in the cross-validation set. These same two randomly determined sets were used throughout all the experiments.

All synaptic weights and threshold values were initialized at the beginning of each training session to small random numbers.

The error-correction learning rule is an iterative process used to update the synaptic weights by a method of gradient descent in which the network minimizes the error as pattern associations (known input-output pairs) in the training set are presented to the network. Each cycle through the training set is known as an epoch. The order or presentation of the pattern associations was the same for all epochs. The learning algorithm consists of six steps which make up the forward pass and the backward pass. In the forward pass, the hidden layer neuron activations are first determined $$h = F(iW1 + \theta_h)$$

where h is the vector of hidden-layer neurons, i the vector of input-layer neurons, W1 the weight matrix between the input and hidden layers, and F( ) the activation function. A logistic function is used as the activation function $$F(x) = \frac{1}{1 + e^{-x}}.$$

Then the output-layer neurons are computed $$o = F(hW2 + \theta_o)$$

where o represents the output layer, h the hidden layer and W2 the matrix of synapses connecting the hidden layer and output layers. The backward pass begins with the computation of the output-layer error $$e_o = (o - d),$$

where d is the desired output. If each element of $e_o$ is less than some predefined training error tolerance vector $TE_{tol}$, than the weights are not updated during that pass and the process continues with the next pattern association. A training error tolerance of 0.1 was used in all experiments unless otherwise specified. Otherwise, the local gradient at the output layer is then computed:

$$g_o = o(1 - o)e_o.$$

Next, the hidden-layer local gradient is computed:

$$g_h = h(1 - h)W2g_o.$$

Once the hidden layer error is calculated, the second layer of weights is adjusted $$W2_m = W2_{m-1} + \Delta W2$$

where $$\Delta W2 = \eta h g_o + \gamma \Delta W2_{m-1}.$$

is the learning rate, $\gamma$ is the momentum factor, and m is the learning iteration. The first layer of weights is adjusted in a similar manner $$W1_m = W1_{m-1} + \Delta W1$$

where $$\Delta W1 = \eta i e + 66\ W1_{m-1}.$$

The forward pass and backward pass are repeated for all of the pattern associations in the training set, referred to as an epoch, 1000 times. At the end of each epoch, the trained network is applied to the cross-validation set.

Several methods were employed to measure the performance of the network's training. Error, E, for each input set was defined as $$E = \sqrt{\frac{1}{N}\sum_{q=1}^{N}(d_q - o_q)^2}.$$

The learning curve is defined as the plot of E versus epoch. The percent classification, $\phi$, describes the percent of the total test set (training and cross-validation) that is correctly classified based on some defined decision boundary, $\beta$. Receiver-Operating Characteristic (ROC) plots have also been utilized to describe trained networks' ability to discriminate between the alternative possible outcome states. In these plots, measures of sensitivity and specificity are shown for a complete range of decision boundaries. The sensitivity, or true-positive fraction is defined as $$\text{sensitivity} = \frac{\text{true positive}}{\text{true positive} + \text{false negative}}$$

and the false-positive fraction, or (1-specificity) is defined as $$(1-\text{specificity}) = \frac{\text{false positive}}{\text{false positive} + \text{true negative}}.$$

These ROC plots represent a common tool for evaluating clinical laboratory test performance.

Using the test set described, experiments were performed to determine if the presence of heparin could be predicted with this method. First, experiments were conducted to determine optimal error-correction backpropagation learning parameters: (1) hidden layer size, (2) learning rate, and (3) momentum. Additional experiments were also conducted to compare the performance of networks based on PT and APT assays alone with that of one combining the results of both, the effect of the training error tolerance, and the decision boundary selection.

FIG. 9 shows the effect of the hidden layer size on the training and cross validation error and the percent correct classification for the optimal decision boundary, defined as the decision boundary which yielded the lowest total number of false positives and false negatives from the total test set. As the hidden layer size is increased, the error is decreased. However, the ability to generalize does not increase after a hidden layer size of 6. The most significant benefit in terms of both error and percentage correct classification is between 4 and 6. A hidden layer size of 6 was used for the remainder of the experiments.

Figure 4:
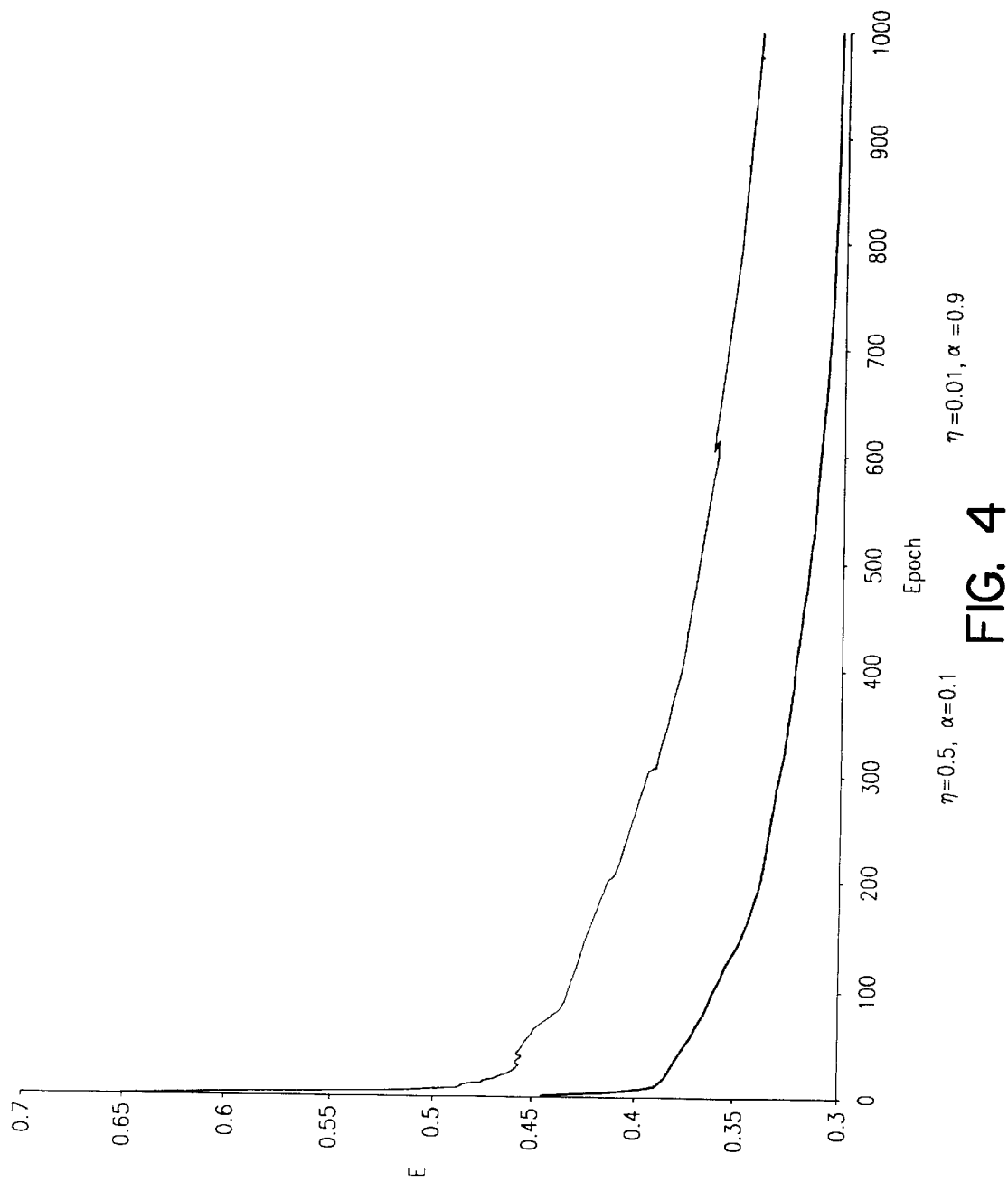
FIG. 4 is an illustration of two learning curves.
Figure 5:
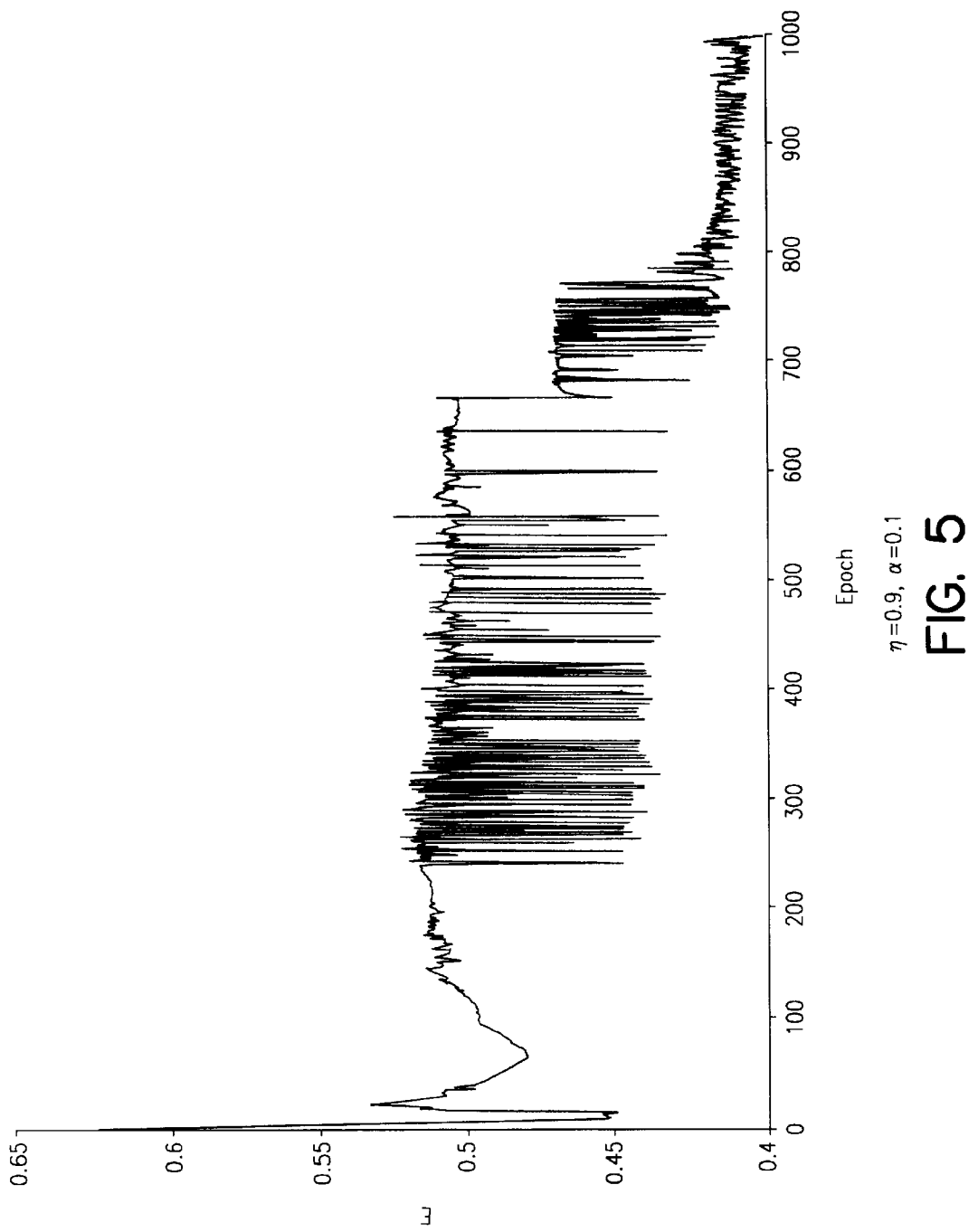
FIG. 5 is an illustration of an unstable learning curve.

A series of experiments were conducted with $\eta=\{0.01, 0.1, 0.5, 0.9\}$ and $\gamma\{0.0, 0.1, 0.5, 0.9\}$. FIG. 4 shows the learning curves for two of the best combinations of parameters. FIG. 5 shows an example learning curve when the learning rate is so high it leads to oscillations and convergence to a higher E. In general, as $\eta \rightarrow 0$ the network converged to a lower E and as $\gamma \rightarrow 1$, the rate of convergence improved. As $\eta \rightarrow 1$, the value of E converged too increased and oscillations increased. In addition, as $\eta \rightarrow 1$, $\gamma \rightarrow 1$ exacerbated the oscillations.

Figure 6:
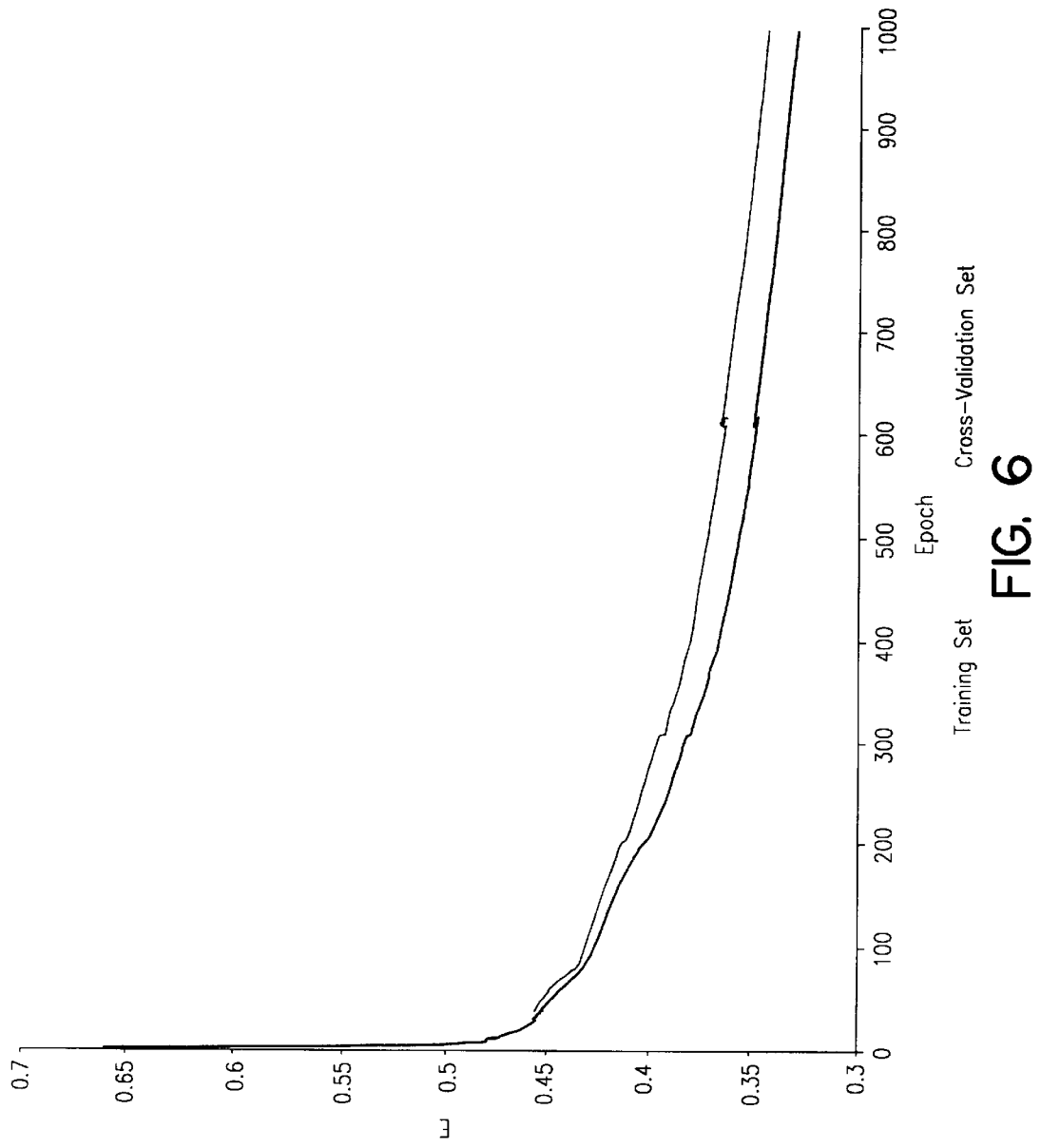
FIG. 6 is a graph showing a comparison of training and cross-validation learning curves.

FIG. 6 shows a comparison of the learning curve for the training set and cross-validation set for $\eta=0.5$ and $\gamma=0.1$. It is a primary concern when developing neural networks, and it has been previously shown that it is important to look not only at the error in the training set for each cycle, but also the cross-validation error.

Figure 7:
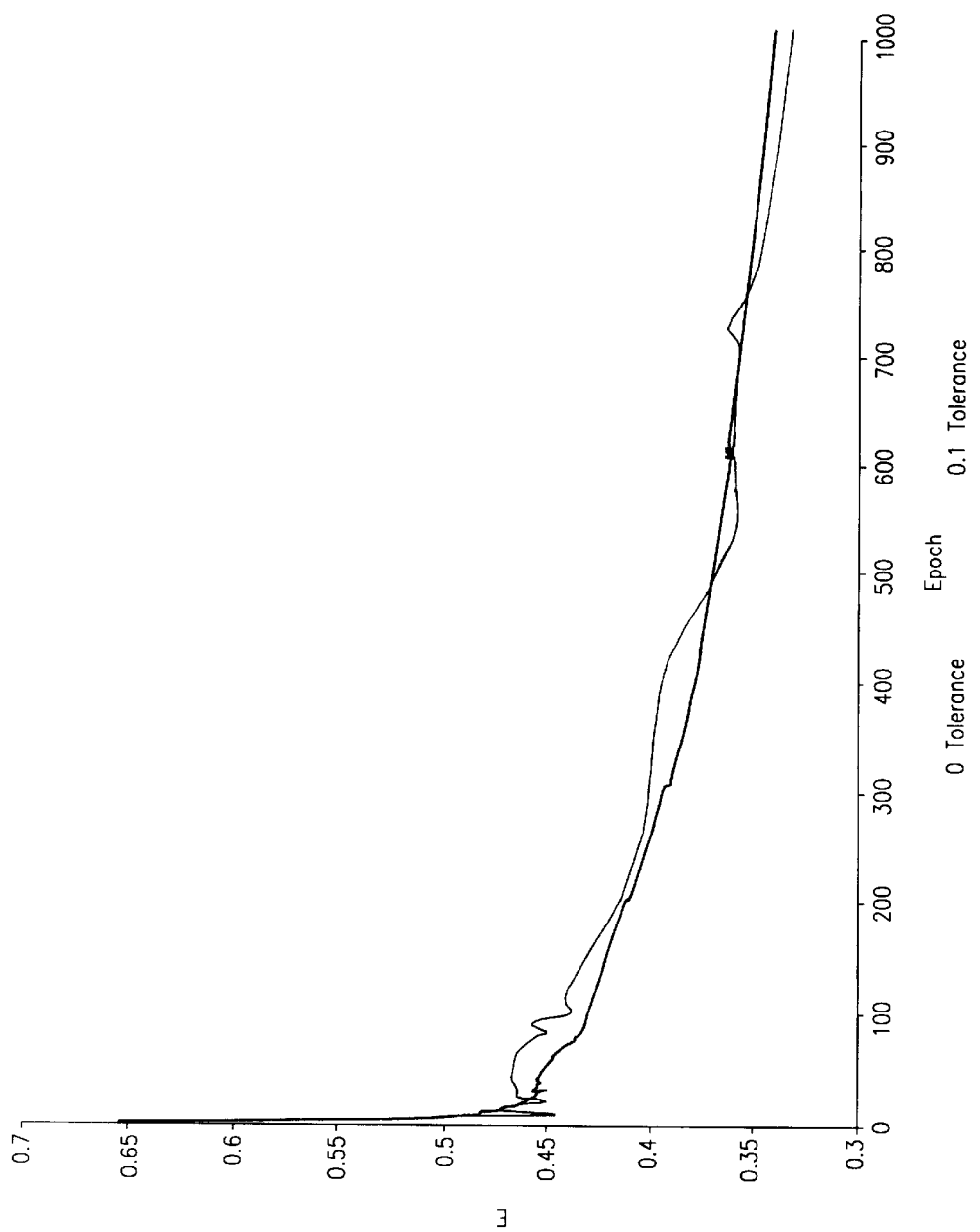
FIG. 7 is a graph showing a comparison of training error for training tolerances of 0.0 and 0.1.

FIG. 7 shows the learning curve $\eta=0.5$ and $\gamma=0.1$ and a learning tolerance of 0.0 and 0.1. These results suggest that a small learning tends to smoothen the convergence of the learning process.

Figure 8:
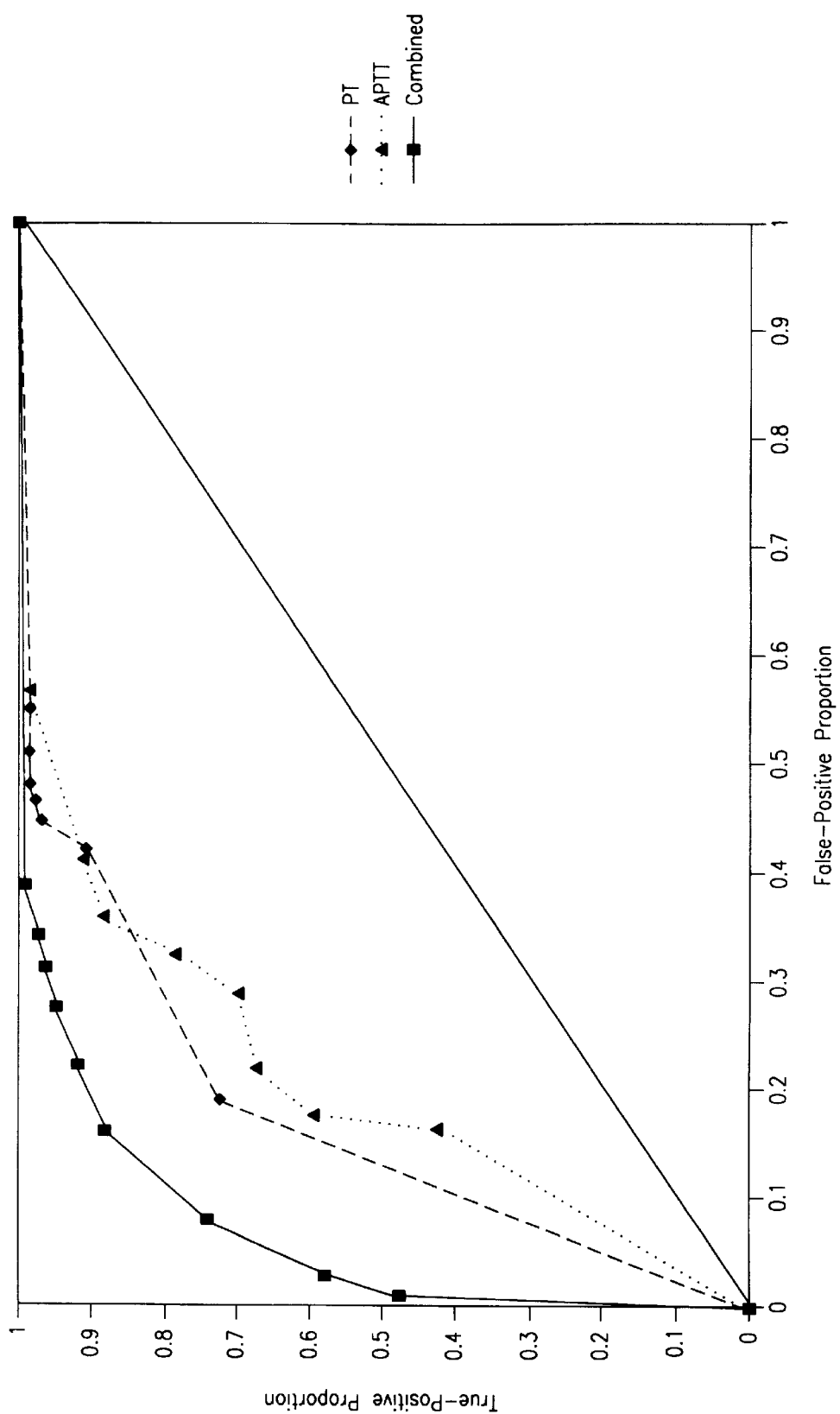
FIG. 8 is a ROC illustrating the effect of decision boundary on classification.

FIG. 8 shows the ROC plot for networks trained with the predictor variables from each of the two screening assays with that of them combined. In the single assay cases, the hidden layer size was 3. While using the data from one assay does lead to some success, using the information from both assays makes a significant improvement in the ability of the network to correctly predict the presence of heparin. This graph indicates that a 90% true positive proportion can be achieved with a false positive proportion of 15%. Using a single assay, a 60–70% true positive proportion can be achieved with a false positive proportion of approximately 15%.

EXAMPLE 2

Factor VIII

Figure 10:
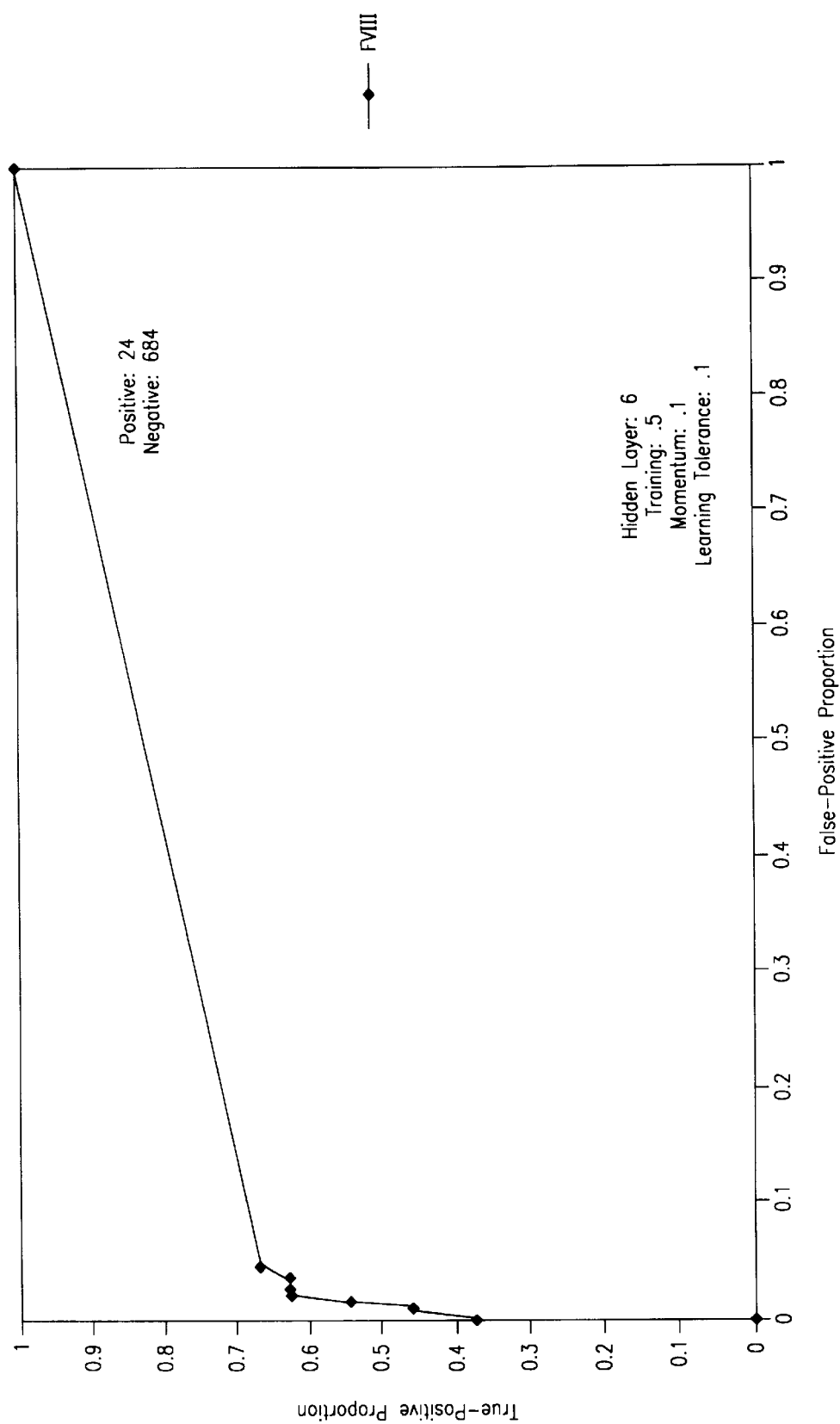
FIG. 10 is a receiver operator characteristic plot related to predicting an abnormality in relation to Factor VIII.
Figure 11:
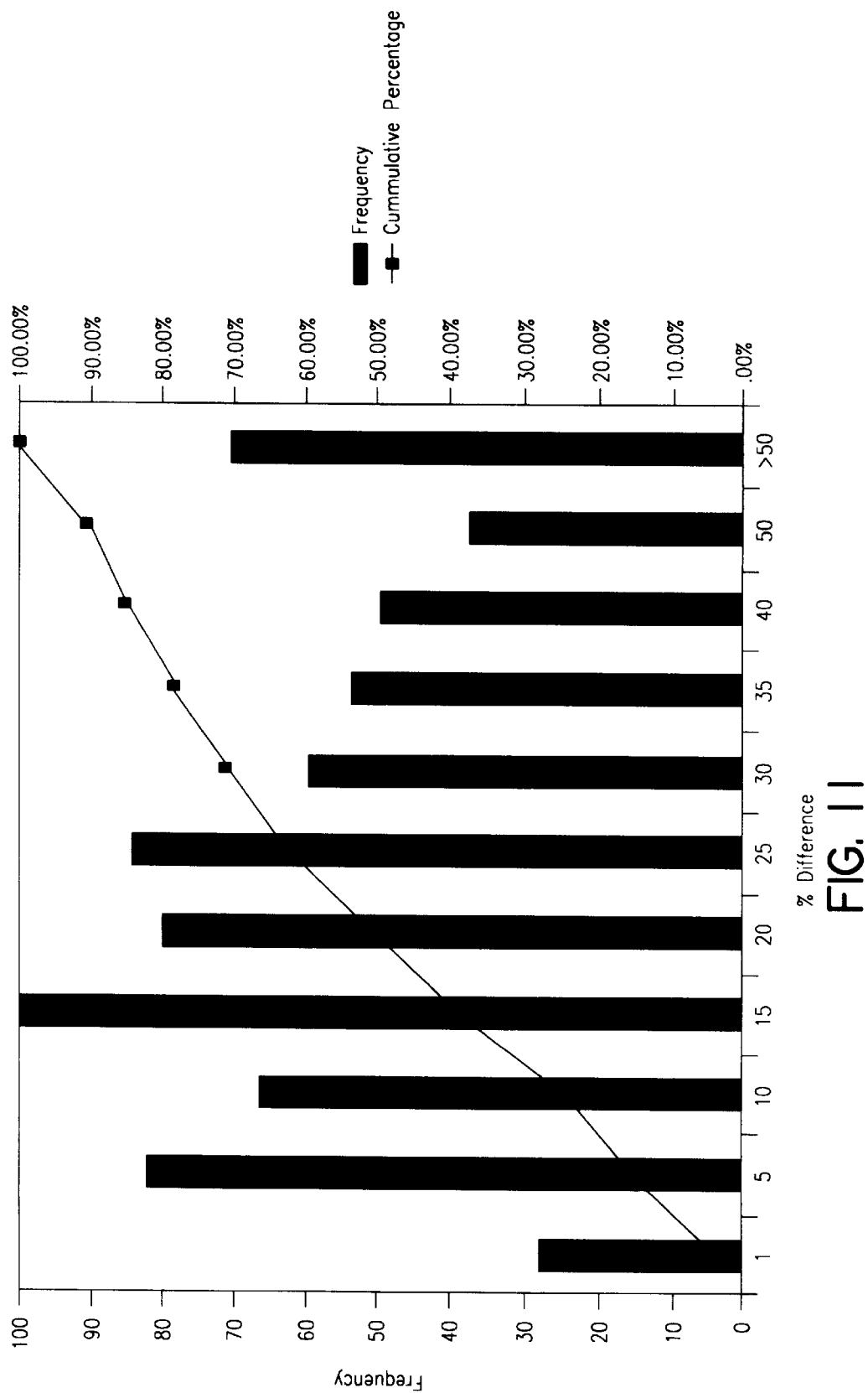
FIG. 11 is a graph demonstrating the ability to predict actual Factor VIII activity.

Similar tests were run as in Example 1. As can be seen in FIGS. 10 and 11, two training sessions were conducted for predicting a Factor VIII condition in an unknown sample. FIG. 10 is a receiver operator characteristic plot related to predicting an abnormality in relation to Factor VIII. In FIG. 10, everything below 30% activity was indicated as positive, and everything above 30% was indicated as negative. Cutoff values other than 30% could also be used. In this Example, the activity percentage has a known accuracy of approximately + or −10%. In FIG. 11, the actual percent activity was utilized as the output.

EXAMPLE 3

Factor X

Figure 12:
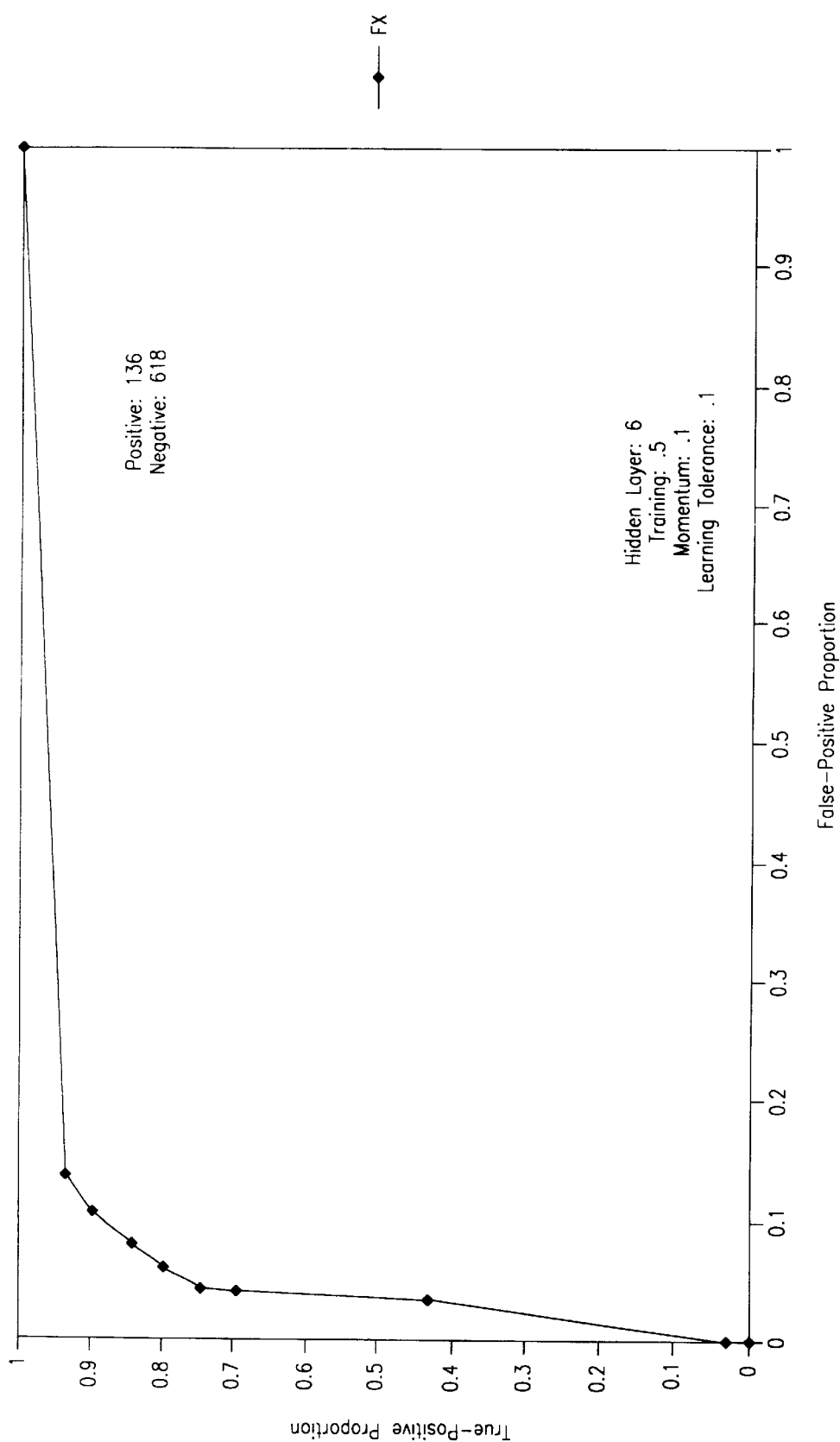
FIG. 12 is a receiver operator characteristic plot related to predicting an abnormality in relation to Factor X.

As can be seen in FIG. 12, the method of the present invention was run similar to that as in Example 2, where here an abnormality in Factor X concentration was predicted from unknown samples. Everything below 30% activity was indicated as positive, and everything above 30% was indicated as negative. Cutoff values other than 30% could also be used.

The results of the cross-validation sample sets throughout the experiments indicate that the sample size was sufficient for the network to generalize. While the random distribution of the training and cross-validation sets were held constant throughout the experiments presented, other distributions have been used. These distributions, while all yielding different results, still lead to the same general conclusion.

Many alternatives for or additions to the set of predictor variables were explored. This included coefficients of a curve fitted to the data profile, pattern recognition, and clot time-based parameters. Low order functions tend to lose information due to their poor fit, and high order functions tend to lose information in their multiple close solutions. Clot-based parameters, such as clot time, slope in the section prior to the initiation of clot formation, and afterwards, are often available, but not always (because in some samples, the clot time is not detectable). The successful results observed indicate that the set of predictor variables used are effective for predicting congenital or acquired imbalances or therapeutic conditions.

The optimization of the network learning algorithm's parameters made significant differences in its performance. In general, performance was best with low learning rates, high momentum rates, some small training error tolerance, and a hidden layer size approximately half of the size of the input layer.

It is to be understood that the invention described and illustrated herein is to be taken as a preferred example of the same, and that various changes in the method and apparatus of the invention may be resorted to, without departing from the spirit of the invention or scope of the claims.

We claim:

1. A method for predicting the presence of at least one congenital or acquired imbalance or therapeutic condition associated with thrombosis or hemostasis from at least one time-dependent measurement profile, comprising;

a) adding one or more reagents to a sample to cause coagulation in said sample and performing at least one time-dependent measurement on said sample by taking a plurality of measurements of a property of said sample over time, which property changes when said sample undergoes coagulation, so as to derive a respective at least one time-dependent measurement profile;

b) defining a set of a plurality of predictor variables which define the at least one time-dependent measurement profile;

c) deriving a model that represents the relationship between the at least one congenital or acquired imbalance or therapeutic condition associated with thrombosis or hemostasis, and the set of predictor variables; and d) utilizing the model of step c) to predict the presence of the at least one congenital or acquired imbalance or therapeutic condition associated with thrombosis or hemostasis in the sample.

2. A method according to claim 1, wherein said at least one time-dependent measurement profile is at least one optical profile.

3. A method according to claim 2, wherein said at least one optical profile is provided by an automated analyzer for thrombosis and hemostasis testing.

4. A method according to claim 2, wherein a plurality of optical measurements at one or more wavelengths are taken over time so as to derive said at least one optical profile, said optical measurements corresponding to changes in light scattering and/or light absorption in the sample.

5. A method according to claim 4, wherein in step a) said sample is automatically removed by an automated probe from a sample container to a test well, said one or more reagents are automatically added to said test well so as to initiate said property changes within said sample, and the change in said property over time is automatically optically monitored so as to derive said at least one optical profile.

6. A method according to claim 5, wherein after step d), the predicted at least one congenital or acquired imbalance or therapeutic condition is automatically stored in a memory of an automated analyzer and/or displayed on said automated analyzer.

7. A method according to claim 5, wherein in step d), one or more assays for confirming the existence of said at least one congenital or acquired imbalance or therapeutic condition is automatically performed.

8. A method according to claim 7, wherein said one or more confirming assays are automatically ordered and performed on an automated analyzer, with results of said one or more assays being stored in a memory of said automated analyzer and/or displayed on said automated analyzer.

9. A method according to claim 2, wherein a plurality of optical measurements are taken over time so as to derive said at least one optical profile, and wherein said plurality of optical measurements are each normalized to a first optical measurement.

10. A method according to claim 2, wherein said at least one optical profile is an optical transmission profile.

11. A method according to claim 10, wherein said optical transmission profile is based on data collected over time that represent the normalized level of light transmission through a sample as a clot forms.

12. A method according to claim 1, further comprising: before step a), providing a set of data from known samples, which data is used in step c) for deriving said model.

13. A method according to claim 12, wherein said set of data from known samples is provided by performing a plurality of assays on said known samples.

14. A method according to claim 12, wherein said model of step c) is a neural network.

15. A method according to claim 1, wherein said relationship in step c) is determined via at least one automated algorithm.

16. A method according to claim 15, wherein said model is a multilayer perceptron, and wherein said at least one automated algorithm is a back propagation learning algorithm.

17. A method according to claim 1, wherein in step a), a plurality of time-dependent measurement profiles are derived for use in step b).

18. A method according to claim 17, wherein said plurality of time dependent measurement profiles includes at least two profiles from assays initiated with prothrombin time reagents activated partial thromboplastin time reagents, fibrinogen reagents and thrombin time reagents.

19. A method according to claim 1, wherein said set of predictor variables includes one or more of: a minimum of the first derivative of the profile, a time index of the minimum of the first derivative, a minimum of the second derivative of the profile, a time index of the minimum the second derivative, a maximum of the second derivative of the profile, a time index of the maximum of the second derivative, an overall change in the coagulation parameter during the time-dependent measurement on the sample, a clotting time, a slope of the profile prior to clot formation, and a slope of the profile after clot formation.

20. A method according to claim 19, wherein three or more of said predictor variables are within said set.

21. A method according to claim 20, wherein more than three of said predictor variables are within said set.

22. A method according to claim 1, wherein said sample is a sample from a medical patient, and wherein in step d), both said model and additional patient medical data are utilized for predicting the presence of said at least one congenital or acquired imbalance or therapeutic condition.

23. A method according to claim 1, wherein said sample is a sample from a medical patient where the at least one congenital or acquired imbalance or therapeutic condition associated with thrombosis or hemostasis is not known, or, if suspected, has not been confirmed.

24. A method according to claim 1, wherein the at least one time-dependent measurement profile is one or more of a prothrombin time profile, a fibrinogen profile, an activated partial thromboplastin time profile, a thrombin time profile, a protein C profile, or a protein S profile.

25. A method for predicting the presence of heparin in a sample, from at least one time-dependent measurement profile, comprising:

a) adding one or more reagents to a sample to cause coagulation in said sample and performing at least one time-dependent measurement on said sample by taking a plurality of measurements of a property of said sample over time, which property changes when said sample undergoes coagulation, so as to derive a respective at least one time-dependent measurement profile;

b) defining a set of plurality of predictor variables which define the data of the at least one time-dependent measurement profile;

c) deriving a model that represents the relationship between the presence of heparin, and the set of predictor variables; and d) utilizing the model of step c) to predict the presence of heparin in the sample.

26. A method according to claim 25, wherein said at least one time-dependent measurement profile is at least one optical profile.

27. A method according to claim 26, wherein said at least one optical profile is provided by an automated analyzer for thrombosis and hemostasis testing.

28. A method according to claim 27, wherein in step a) said sample is automatically removed by an automated probe from a sample container to a test well, said one or mere reagents are automatically added to said test well so as to initiate said property changes within said sample, and the chance in said property over time is automatically optically monitored so as to derive said at least one optical profile.

29. A method according to claim 28, wherein after step d), a predicted presence of heparin is automatically stored in a memory of said automated analyzer and/or displayed on said automated analyzer.

30. A method according to claim 28, wherein in step d), one or more assays for confirming the existence of heparin in the sample is automatically performed.

31. A method according to claim 30, wherein said one or more confirming assays are automatically ordered and performed on said automated analyzer, with results of said one or more confirming assays being stored in a memory of said automated analyzer and/or displayed on said automated analyzer.

32. A method according to claim 26, wherein a plurality of optical measurements at one or more wavelengths are taken over time so as to derive said at least one optical profile, said optical measurements corresponding to changes in light scattering and/or light absorption in the sample.

33. A method according to claim 26, wherein a plurality of optical measurements are taken over time so as to derive said at least one optical profile, and wherein said plurality of optical measurements are each normalized to a first optical measurement.

34. A method according to claim 25, further comprising: before step a), providing a set of data from known samples, which data is used in step c) for deriving said model.

35. A method according to claim 34, wherein said data from known samples is provided by performing a plurality of assays on said known samples.

36. A method according to claim 34, wherein said model of step c) is a neural network.

37. A method according to claim 25, wherein said relationship in step c) is determined via at least one automated algorithm.

38. A method according to claim 37, wherein said model is a multilayer perceptron, and wherein said at least one automated algorithm is a back propagation learning algorithm.

39. A method according to claim 25, wherein in step a), a plurality of time-dependent measurement profiles are derived for use in step b).

40. A method according to claim 39, wherein said plurality of time dependent measurement profiles includes at least two profiles from assays initiated with prothrombin time reagents, activated partial thromboplastin time reagents, fibrinogen reagents and thrombin time reagents.

41. A method according to claim 25, wherein said set of predictor variables includes one or more of: a minimum of the first derivative of the profile, a time index of the minimum of the first derivative, a minimum of the second derivative of the profile, a time index of the minimum of the second derivative, a maximum of the second derivative of the profile, a time index of the maximum of the second derivative, an overall change in the coagulation parameter during the time-dependent measurement on the sample, a clotting time, a slope of the profile prior to clot formation, and a slope of the profile after clot formation.

42. A method according to claim 41, wherein three or more of said predictor variables are within said set.

43. A method according to claim 42, wherein more than three of said predictor variables are within said set.

44. A method according to claim 25, wherein said sample is a sample from a medical patient, and wherein in step d), both said model and additional patient medical data are utilized for predicting the presence of heparin in said sample.

45. A method according to claim 25, wherein the time dependent measurement profile is one or more of a prothrombin time profile, a fibrinogen profile, an activated partial thromboplastin time profile, a thrombin time profile, a protein C profile, or a protein S profile.

46. A method according to claim 25, wherein said sample is a sample from a medical patient where the presence of heparin is not known, or, if suspected, has not been confirmed.

47. A method according to claim 26, wherein said at least one optical profile is an optical transmission profile.

48. A method according to claim 47, wherein said optical transmission profile is based on data collected over time that represent the normalized level of light transmission through a sample as a clot forms.

* * * * *